(12) United States Patent
Boborodea et al.

(10) Patent No.: US 7,389,678 B2
(45) Date of Patent: Jun. 24, 2008

(54) COLUMN FOR ANALYTICAL TEMPERATURE RISING ELUTION FRACTIONATION (ATREF)

(75) Inventors: Adrian-Gelu Boborodea, Louvain-la-Neuve (BE); Christian Bailly, Antwerp (BE); Daniel Daoust, Chaumont-Gistoux (BE); Alain Jonas, Louvain-la-Neuve (BE); Bernard Nysten, Sauvenière (BE)

(73) Assignee: Université Catholique de Louvain, Loucain-La-Neuve (BE)

( * ) Notice: Subject to any disclaimer, the term of this patent is extended or adjusted under 35 U.S.C. 154(b) by 11 days.

(21) Appl. No.: 10/530,781

(22) PCT Filed: Oct. 7, 2003

(86) PCT No.: PCT/EP03/11044

§ 371 (c)(1),
(2), (4) Date: Apr. 7, 2005

(87) PCT Pub. No.: WO2004/034047

PCT Pub. Date: Apr. 22, 2004

(65) Prior Publication Data

US 2005/0271545 A1    Dec. 8, 2005

(30) Foreign Application Priority Data

Oct. 9, 2002    (EP)    .................... 02447193

(51) Int. Cl.
*G01N 30/60*    (2006.01)
(52) U.S. Cl. .................................... 73/61.53
(58) Field of Classification Search ............... 73/61.53, 73/61.52, 53.01, 61.43
See application file for complete search history.

(56) References Cited

U.S. PATENT DOCUMENTS

| | | | | |
|---|---|---|---|---|
| 3,225,520 A | | 12/1965 | Burow | |
| 3,340,085 A | * | 9/1967 | Halasz et al. | 502/400 |
| 3,492,794 A | * | 2/1970 | Petersen et al. | 96/101 |
| 4,798,081 A | * | 1/1989 | Hazlitt et al. | 73/53.01 |
| 5,030,713 A | * | 7/1991 | Wild et al. | 528/482 |
| 5,800,706 A | * | 9/1998 | Fischer | 210/198.2 |
| 6,770,355 B1 | * | 8/2004 | Minami et al. | 428/220 |
| 6,780,314 B2 | * | 8/2004 | Jinno et al. | 210/198.2 |
| 2002/0050470 A1 | * | 5/2002 | Jinno et al. | 210/198.2 |

OTHER PUBLICATIONS

Britto et al., "High Density Polyethylene Fraction with Supercritical Propane," Journal of Polymer Science: Part B Polymer Physics, vol. 37, 553-560 (1999).*

(Continued)

*Primary Examiner*—Hezron E. Williams
*Assistant Examiner*—Paul M West
(74) *Attorney, Agent, or Firm*—Knobbe, Martens, Olson & Bear, LLP (57) ABSTRACT

The present invention relates to a column for performing analytical temperature rising elution fractionation (ATREF) characterized in that the packing of said column comprises elastic wires having a good elasticity and a good thermal conductivity. The present invention also relates to a device comprising the column according to the invention, a temperature controlling system for controlling the temperature of said column, a sample injector for injecting a polymer sample solution into said column, a pump for eluting the polymer fractions from said column and a detector for detecting eluting fractions of said sample solution. The present invention further relates to a method for performing ATREF analyses using the column according to the invention.

12 Claims, 5 Drawing Sheets

OTHER PUBLICATIONS

Soars, et al. "Temperature Rising Elution Fractionation of Linear Polyolefins," *Polymer*, vol. 36, No. 8, pp. 1639-1654, 1995.

Wang, et al. "Microstructures of a Highly Short-Chain Branched Polyethylene," *Polymer*, vol. 42, pp. 1733-1741, 2001.

International Search Report.

* cited by examiner

COLUMN FOR ANALYTICAL TEMPERATURE RISING ELUTION FRACTIONATION (ATREF)

FIELD OF THE INVENTION

In a first aspect the present invention relates to a column for performing analytical temperature rising elution fractionation (ATREF). In a second aspect the present invention relates to a method for performing ATREF analyses using the column according to the invention.

BACKGROUND

Polymers are basically heterogeneous materials, heterogeneity being exhibited through a variety of ways such as distribution of chain lengths, differences in chemical composition from chain to chain, and through the architecture of the chain as tacticity or as in branched and cross-linked structures. Branching may be characterized as long chain branching (LCB) or short chain branching (SCB).

Temperature rising elution fractionation (TREF) is a technique for analysis of crystalline and semi-crystalline polymers by separating the fractions according to crystallizability. TREF has utility to evaluate structure heterogeneity and enables to characterize the distribution of SCB. Elution during TREF is governed by the melting of semi-crystalline polymers in the presence of a solvent. Fractionation is expected to run similar to solid state melting and can be quantitatively correlated with the solid state melting.

Preparative TREF (PTREF) is performed to isolate polymer fractions for further investigations. This technique has certain disadvantages. During this process, a high quantity of solvent for eluting the sample and also a high quantity of non-solvent, usually methanol, for precipitation of eluting fractions, are required. Also this technique is very time-consuming as it takes several days to perform a fractionation.

An improvement upon the PTREF method was the development of analytical temperature rising elution fractionation (ATREF). ATREF overcomes the limitations of preparative TREF by considerably reducing the column and sample size and by continuously monitoring the amount of the eluted polymer fractions, as a function of column temperature using an on-line detector. The ATREF technique provides a crystallizability fractionation profile, which is the concentration of species eluting at a specified temperature. In ATREF the polymers to be analyzed are dissolved in a suitable hot solvent and allowed to crystallize in a column by slowly reducing the temperature. The crystallized polymer sample is eluted from the column by slowly increasing the temperature of the column. The concentration of the polymeric solution eluted from the column is detected with an on-line detector. A TREF chromatogram curve is then generated. ATREF can be applied for analyzing crystalline and semi-crystalline polymers, such as (poly)propylene (PP), (poly)ethylene (PE) and their copolymers. For semi-crystalline polymers, ATREF also provides an elution profile for the species that cannot crystallize. This amorphous portion of the polymer appears as a first peak when the elution process is started.

Existing methods for ATREF typically use an infrared (IR) detector as concentration detector for eluted fractions. In general, IR detectors offer good baseline stability for both high variations of temperature and pressure during the elution process. However, this type of detector has a poor sensitivity and consequently requires the use of large amounts of polymers in analyses. Furthermore, IR detectors are not available on commercial equipment and are complicated to install.

Differential refractive index (DRI) detectors are a valuable alternative for IR detectors as they are more sensitive than IR detector. U.S. Pat. No. 4,798,081 describes a method for performing ATREF wherein detection is done using a DRI detector. The document relates to a method and apparatus for coupling high temperature continuous viscometry (HTCV) with analytical temperature rising elution fractionation (ATREF) for analysis of crystalline and semi-crystalline polymers. The method and apparatus provide a crystallinity (or density or branching number) versus weight percent profile concurrently with viscosity average molecular weight for each incremental crystalline fraction. The concentration detector may be a differential refractometer, for measuring relative changes in the concentration of the solution. However, this document describes a method for performing ATREF with DRI detector which is complex and which requires intensive manual operations.

Existing methods for ATREF require that the solvent flow through the column is stopped during the crystallization of the polymer. This unavoidably leads to a poor baseline stability upon restarting of the flow during the elution of the polymer.

There remains a great need in the art for a method and apparatus for ATREF analysis, which overcomes the drawbacks of the known methods. The present invention relates to an improved apparatus and method suitable for performing ATREF analyses.

SUMMARY OF THE INVENTION

In a first aspect the invention relates to a column for use in an analytical temperature rising elution fractionation (ATREF) analysis of a crystalline or a semi-crystalline polymer sample solution characterized in that the packing of said column comprises elastic wires.

"ATREF analysis" comprises the analysis of a polymer sample, which is first dissolved in a suitable solvent and allowed to crystallize in a column by reducing the temperature. The crystallized polymer fractions are subsequently eluted from the column by increasing the temperature of the column. The concentration of the eluted solution from the column is measured with an on-line detector, and a TREF chromatogram curve, i.e. a graphical presentation of the detector response, is generated representing the composition profile of the polymer sample fractions having different crystallizability. The main elements of an ATREF analysis system comprise an injector, a pump, a column, and a detector, connected to a computer system for recording and representing the sample data in a chromatogram.

The term "column" as used herein refers to a tube and the packing, i.e. a solid support, contained within. According to the present invention, the column is made of stainless steel, glass, ceramic, or a polymer, and has an internal diameter less than 20 mm and a length comprised between 50 and 500 mm. The column can be provided within an ATREF system and is connected with a sample injector, a pump and a detector, and in particular a DRI detector. Also, the column is provided within a temperature controlling means.

The packing of the column according to the present invention comprises elastic wires. The term "elastic wires" as used herein refers to wires, which can be made of any non-corrodible material, having a good elasticity, i.e. having a Young modulus higher than 50 GPa, and a good thermal conductivity, i.e. having a thermal conductivity higher than 0.1 W/cm/K. Particularly preferred are elastic wires made of stainless steel, metal, carbon fibers or glass fibers. During the ATREF process a crystallized polymer sample will be withheld in the packing, and the wires are thus used as a support for the crystallized fractions of polymer.

In a second aspect the present invention relates to a device for use in an analytical temperature rising elution fractionation analysis comprising the column according to the invention, a temperature controlling system for controlling the temperature of said column, a sample injector for injecting a polymer sample solution into said column, a pump for eluting the polymer fractions from said column and a detector for detecting eluting fractions of said sample solution.

The present invention provides a column, which is particularly suitable for use during ATREF analysis since the column according to the invention considerably improves the baseline stability of the detector, used during the ATREF. The baseline of a detector refers to the portion of the chromatogram recording the detector response when only the mobile phase, i.e. the eluent, emerges from the column. Baseline stability refers to substantial absence of variation in the chromatogram when only eluent emerges from the column. Surprisingly, according to the present invention the improvement of the baseline stability of the detector is essentially due to the use of elastic wires as column packing. These elastic wires exert a double effect. The packing of the column with elastic wires provides an excellent thermal conductivity to the column, and the elastic wires inside the column compensate for the pressure variation during the elution process.

In particular, the column according to the invention is particularly suitable for use during ATREF analyses with a differential refractive index (DRI) detector. A DRI detector continuously measures the difference in refractive index between the mobile phase consisting of pure solvent and the mobile phase consisting of polymer dissolved in pure solvent. The column according to the invention improves the baseline stability to such a point that a DRI detector can be used instead of a less sensitive IR detector for ATREF analysis.

In addition, the use of a packed column according to the invention that allows the use of a sensitive DRI detector during ATREF, further enables to reduce the quantity of polymer necessary for the ATREF analysis. A considerable reduction of the amount of polymer injected in the column during ATREF is an important feature as it involves several favorable consequences. As a smaller amount of polymers needs to be injected, a higher dilution of the polymers in the column designed according to the invention is obtained, which provides a better separation quality. Furthermore, a reduction of the amount of polymer injected in the column involves the possibility to reduce the time necessary for crystallization of different fractions. Because the crystallization step is the most time consuming during the analysis, this feature reduces the time necessary for analysis. Finally, the appearance of spurious peaks and artifacts in the chromatogram, caused by an excess amount of polymer used during the analysis, is essentially reduced.

In a third aspect the present invention relates to a method for ATREF analysis using the column according to the invention. In particular, the invention relates to a method for performing an ATREF analysis of a crystalline or a semi-crystalline polymer solution comprising the steps of:

injecting a sample of said polymer solution into the column according to the invention, crystallizing said polymer sample solution in said column over a cooling temperature gradient to produce a crystallized polymer sample while keeping solvent flowing through said column;

eluting said crystallized polymer sample by increasing the temperature of said column over a heating temperature gradient to produce eluted fractions of the polymer sample solution, said fractions being eluted in function of the temperature; and measuring the concentration of the eluted fractions of polymer sample solution by means of a detector.

In a preferred embodiment, the invention relates to a method wherein said detector is a differential refractive index detector.

Since the column according to the invention enables to reduce the necessary quantity of polymer and the volume of polymer solution for ATREF analysis, the injection of the polymer sample solution in the column can be performed automatically. Furthermore, the column according to the invention can easily be provided within a temperature control system, with only minor modification of a high temperature gel permeation chromatography (GPC) system and a temperature control system. As a result the manual removal of the column from the solvent flow is not required anymore during the crystallization step. Also, the method according to the invention enables to keep solvent flowing through the column during the crystallization step of the ATREF analysis. This is relevant for the automation of the ATREF process and the invention thus provides a method for performing ATREF analyses, which can be performed in an easy and completely automated way. Moreover, the possibility to perform completely automated ATREF analyses further enables to considerably reduce analysis time.

Other objects and advantages of the present invention will become apparent from the following detailed description and the accompanying drawings.

DETAILED DESCRIPTION OF THE FIGURES

FIG. 2 illustrates the chromatogram of a standard LDPE sample analyzed with the ATREF method using two type of columns. FIG. 2A represents the chromatogram of the LDPE sample obtained with the 0.39×15 cm column packed with $Al_2O_3$, while

FIG. 5 illustrates the TREF chromatogram of a PP sample analyzed with the ATREF method using two types of columns. FIG. 5A represents the TREF chromatogram of the PP sample obtained with 0.39×15 cm column packed with $Al_2O_3$, while

DETAILED DESCRIPTION OF THE INVENTION

The present invention relates to a new fractionation column for use during ATREF analysis. ATREF is a particular type of column chromatography. In general, "chromatography" is a physical method of separation in which the components to be separated are distributed between two phases, one of which is stationary, the stationary phase, while the other, the mobile phase, moves in a definite direction. In ATREF analysis, the stationary phase is comprised within the column and consists of a packing, the mobile phase consists of the eluent.

As mentioned above, "ATREF" consists of a fractionation technique, which provides a composition fractionation profile, being the concentration of fractions of the polymer sample eluting at a specified temperature. In ATREF the polymers to be analyzed are dissolved in a suitable hot solvent, and allowed to crystallize in a column by slowly reducing the temperature. In the second step fractions of the crystallized polymer sample are eluted from the column in function of the temperature by slowly increasing the temperature of the column. The concentration of these fractions is determined by the on-line built-in detector and a TREF chromatogram is generated.

Column for Use in ATREF

In a first embodiment, the present invention relates to a column for use in an analytical temperature rising elution fractionation analysis of a crystalline or a semi-crystalline polymer sample solution characterized in that the packing of said column comprises elastic wires.

The column according to the invention is preferably made of stainless steel, glass, ceramic or a polymer. Columns made of these kinds of materials are particularly suitable for use in ATREF analysis since they resist high temperature and pressure variations and are inert to the solvent. In an embodiment, the column according to the invention has an internal diameter less than 20 mm and a length comprised between 50 and 500 mm, and preferably between 100 and 300 mm. Consequently, according to these characteristics the column according to the invention is compact and easy to handle.

Column Packing

One of the innovative aspects of the column according to the invention comprises its packing. Where traditional column packings of fractionation columns consist of metallic shots or metallic plates, the present column is provided with a particular type of packing, i.e. a packing comprising elastic wires. The term "elastic wires" refers to small, fiber-like objects, which can be made of any non-corrodible material. Preferred are elastic wires made of stainless steel, metal, carbon fibers or glass fibers. Preferred metals include stainless steel, gold, silver, copper or aluminum. The elastic wires have a length of at least 1.5 mm and preferably at least 2 mm, and a diameter of less than 1 mm. In another embodiment, the column according to the present invention is provided with a packing comprising elastic wires having a length per diameter (L/D) of at least 3 and preferably at least 10, and even more preferably at least 50.

The elastic wires have a good elasticity. The elastic properties of a material determine how much the material will deform under a given amount of external force. Elastic properties are represented by the Young modulus or elasticity modulus. In a preferred embodiment, the packing of the column comprises elastic wires, which have Young modulus, higher than 50 GPa.

The elastic wires according to the invention also have a good thermal conductivity. The thermal conductivity, expressed in watts (W) per meter per degree Kelvin, is defined as the quantity of heat energy which is transmitted though a unit length in a unit time when there is a unit temperature difference between the two ends of the length. In another embodiment of the invention, the packing of the column comprises elastic wires, which have a thermal conductivity higher than 0.1 W cm$^{-1}$ K$^{-1}$.

The use of elastic wires as column packing instead of small metal particles, shots or plates is a novel approach. Due to the use of elastic wires, the column has an excellent thermal conductivity and the elastic wires inside the column compensate the pressure variation during the elution process. The packing with the elastic wires improves the baseline stability and consequently enables the use of a sensitive DRI detector during ATREF.

The term "baseline stability" of a detector refers to the absence of any perturbation on the detector output that is not related to an eluted solute. It is correlated with detector noise in the sense that higher baseline stability is equivalent to a lower noise. Detector noise is an important characteristic of a detector as it determines the ultimate sensitivity of the device. Detector noise has been divided into short-term noise, which consists of baseline perturbations that have a frequency significantly higher than that of the eluted peak, and long term noise, which consists of baseline perturbations that have similar frequency to the eluted peaks. The quantitative assessment of detector noise is taken as the maximum amplitude of the combined short and long-term noise over a period of time. The column according to the invention reduces the long-term noise, which is the most important type of noise because it cannot be differentiated from an eluted peak of the same amplitude.

Preparation of the Column

The elastic wires were cut to obtain a length per diameter higher than 50. These small wires were manually introduced in the column, and then compressed in the column to occupy about 20% of the total internal volume of the column.

Device for Use in ATREF

In another embodiment, the present invention relates to a device for use in an analytical temperature rising elution fractionation analysis comprising the column according to the invention, a temperature controlling system for controlling the temperature of said column, a sample injector for injecting a polymer sample solution into said column, a pump for eluting the polymer fractions from said column and a detector for detecting eluting fractions of said sample solution.

According to the invention, the device for use in a ATREF system mainly consists of (a) an injector system, for injecting the polymer sample into the column, (b) a pump which maintains a constant flow rate during the crystallization and elution of a sample, c) a column, and (d) a detector, connected to a computer system for recording and representing the sample data in a chromatogram. In particular, the column according to the invention, used for ATREF is connected to the injector system, to the pump, and to the detector and is provided within a temperature-controlling system.

Various temperature-controlling systems, which can provide a good and reproducible temperature program in a large domain, are suitable. Examples of such temperature-controlling systems include but are not limited to an oven or a water or oil bath. The column according to the invention can easily be provided within a temperature controlling system, being e.g. an oil bath, with only minor modification of said temperature controlling device. Said temperature-controlling device provides a controllable cooling and heating profile to the column, which improves the automation of the ATREF system in which the column is provided.

In an embodiment of the invention, a device is provided wherein the column according to the invention is connected to a detector for detecting eluting fractions of said sample solution. The column according to the invention is particularly suitable for use during ATREF analyses with a differential refractive index (DRI) detector. A DRI detector continuously measures the difference in refractive index between the mobile phase consisting of pure solvent and the mobile phase consisting of polymer dissolved in pure solvent. This type of detector requires low pressure variations during the elution process in order to obtain a good baseline stability. Taking the characteristics of the column according to the invention into consideration, it is clear that the present column is very suitable for use with a DRI detector. In fact, the column according to the invention improves the baseline stability to such a point that a DRI detector can be used instead of a less sensitive IR detector for ATREF analysis.

The use of the column according to the present invention for ATREF provides many advantages. The improved baseline stability of the sensitive DRI detector enables to drastically reduce the amount of polymer solution injected in the column during ATREF. As a consequence, a higher dilution of the polymers can be obtained and the volume of polymer injected in the column can be reduced. Furthermore the column for ATREF according to the invention allows to decrease the concentration of the polymer in the column at least 100 times versus conventional known ATREF methods. Also, in the traditional method, the excess amount of polymer used may cause the appearance of spurious peaks and artifacts in the obtained chromatogram; this is substantially avoided by using the column according to the invention. All these features highly favor the separation of the different fractions and provide a clearer composition fractionation profile.

Method for Performing ATREF

In another embodiment, the present invention relates to a method for performing an ATREF analysis of a crystalline or a semi-crystalline polymer solution comprising the steps of:
- injecting a sample of said polymer solution into the column according to the invention,
- crystallizing said polymer sample solution in said column over a cooling temperature gradient to produce a crystallized polymer sample while keeping the solvent flowing through said column;
- eluting said crystallized polymer sample by increasing the temperature of said column over a heating temperature gradient to produce eluted fractions of the polymer sample solution, said fractions being eluted in function of the temperature; and
- measuring the concentration of the eluted fractions of polymer sample solution by means of a detector.

In preferred embodiment, the concentration of the eluted fractionated polymer sample solution is measured in the method according to the invention using a DRI detector. In another preferred embodiment, the column according to the invention is provided within a temperature controlling system.

As mentioned above, the method according to the invention enables to perform ATREF analyses in completely automated way. Several features are crucial for the automation of the ATREF process according to the invention. One feature involves the fact that the column according to the invention used during the ATREF analyses, enables to keep the solvent flowing through the column during the crystallization step. The column according to the invention can easily be provided within a temperature control system, being f.e. an oil bath, with only minor modification of said temperature controlling device. As a result the separation of the column from the solvent flow is not required anymore and the solvent stream does not need to be interrupted during the ATREF analysis. This is relevant for the automation of the ATREF process. Moreover, since the solvent flow is not interrupted, a poor quality of the baseline upon restarting the flow is avoided. Another feature involves the reduction of the amount of polymer required for ATREF analysis when using the column according to the invention. This enables to perform the injection of the polymer samples in an automated way.

Another advantage of the method according to the invention involves the possibility to analyze different polymers. Due to the fact that the column according to the present invention enables a baseline stability of the detector over a large domain of temperatures higher than 135° C., it becomes possible to perform ATREF analyses not only on polyethylene but also on polypropylene, polyester or other crystalline or semicrystalline polymer samples.

In an embodiment, the invention relates to a method wherein an amount of polymer lower than 2 mg polymer, and preferably between 0.2 mg and 1.0 mg polymer is injected into the column according to the invention.

In another embodiment, the method according to the invention enables the injection of a volume of polymer solution lower than 1 ml, and preferably between 0.05 and 0.5 ml.

Reducing the amount of polymer and the volume of polymer solution to be injected in the column enables to completely automate the injection process of the sample to be analyzed. Therefore, in another embodiment, the invention relates to a method wherein the polymer sample solution is automatically injected into the column. For example, this automated injection can be realized using a built-in injector system. Automated injection further improves the reproducibility of the analysis. In a further embodiment, said polymer sample solution is injected automatically at a flow rate lower than 2.0 mL/min. and preferably between 0.1 to 1.0 mL/min.

In a further embodiment, the invention relates to a method wherein the crystallization of said polymer sample solution in said column is performed over a cooling temperature gradient with a maximum temperature up to 210° C., and preferably comprised between 35° C. and 135° C. In another embodiment, the invention relates to a method wherein the crystallization of said polymer sample solution in said column is performed at a cooling rate higher than 0.5° C. per minute. The cooling step induces the crystallization of the polymer samples. The possibility to install rapid cooling conditions enables to reduce analysis time up to 5 to 8 hours, being the complete time for injection and analysis. For comparison so far known ATREF analyses require an analysis time of 12 hours to several days.

In traditional ATREF due to the low sensitivity of the infra-red detector a quantity of injected polymer of 10-15 mg is required, instead of 0.2-1.0 mg necessary when using the column according to the invention. More importantly, in traditional ATREF, the column is completely filled with injected solution of about 10 mg/mL, whereas in the present method the injected solution is further diluted in the crystallization step in the column according to the invention to obtain a concentration of 0.02-0.1 mg/mL. The high difference in concentrations between the traditional method and the present method explains the difference in times required for the crystallization step in the column. Due to this fact, in the present method a cooling gradient can be applied, which is faster than the usually applied cooling rates of 2 to 15° C./hour. Using a cooling rate of 60° C./hour, the time necessary for the cooling step is reduced at least 4 times, which further improves the productivity of the method, including the number of analyses per unit of time.

In another embodiment, the invention relates to a method wherein elution of crystallized polymer sample is performed by increasing the temperature of said column over a heating temperature gradient with a maximum temperature up to 210° C., and preferably comprised between 35° C. and 135° C. The invention further relates to a method wherein the elution step is performed by increasing the temperature of said column at a heating rate higher than 0.5° C. per minute. The temperature increase induces melting of the crystallized fractions of polymer sample in the column. These fractions are solved in the solvent and eluted from the column with a flow rate comprised between 0.1 and 1.0 mL per minute. A suitable solvent involves e.g. trichlorobenzene, dichlorobenzene or xylene. Fractions of the polymer sample solution elute in function of the temperature. The used heating profile and flow rates enable to reduce the necessary quantity of solvent 3 to 5 times. In traditional ATREF the concentration of the solution in the column (10 mg/mL) is at least 100 times higher than in the column according to the invention (0.02-0.1 mg/mL). In the heating step, the low concentration of the melt polymer solution allows to use smaller flow rates of 0.5 to 1.0 mL/min instead of 3 mL/min. The heating step is the crucial step for the solvent consumption. For a heating profile of 1° C./min, about 100 minutes are necessary to perform the elution of sample, which implies, for the above mentioned difference between flow rates, that an amount of solvent 3 to 5 times higher in the traditional ATREF than in the method using the column according to the invention.

The present invention relates to an analytical method for analysis of crystallization, precipitation or extraction of soluble compounds as well as for studying crystallization kinetics. More particularly, the present application relates to an analytical method for analysis of the solutions of crystalline or semi-crystalline polymers such as the analysis of distribution of short chain branches (SCB) in linear low-density polyethylenes, and structural heterogeneity of polypropylene or PP-EP co-polymers.

EXAMPLES

The following examples are meant to illustrate the invention. These examples are presented to exemplify the invention and are not to be considered as limiting the scope of the invention.

Example 1

ATREF Analysis of a Standard Polyethylene Sample

To illustrate the improvements determined by the column according to the invention a low density standard polyethylene (LDPE) provided by National Bureau of Standards (NBS 1476 branched polyethylene) was analysed in an ATREF analysis using a column according to the invention. The column consisted of a stainless steel column having 0.8 cm in diameter and 25 cm in length filled with elastic wires. The wires are made of stainless steel having a diameter of 0.1 mm and an average length of 10 mm. The LDPE sample was injected at a concentration of 3.2 mg/ml. For comparison, the same sample was analysed in an ATREF analysis using a traditional column, being a stainless steel column with 0.39 cm internal diameter and 15 cm in length and packed with small aluminium oxide particles having a 70-230 mesh-size. The LDPE sample was injected at a concentration of 6.3 mg/ml. As detector for ATREF, a built in differential refractive index (DRI) detector of a Waters GPC 150CV system was used.

Figure 1A:
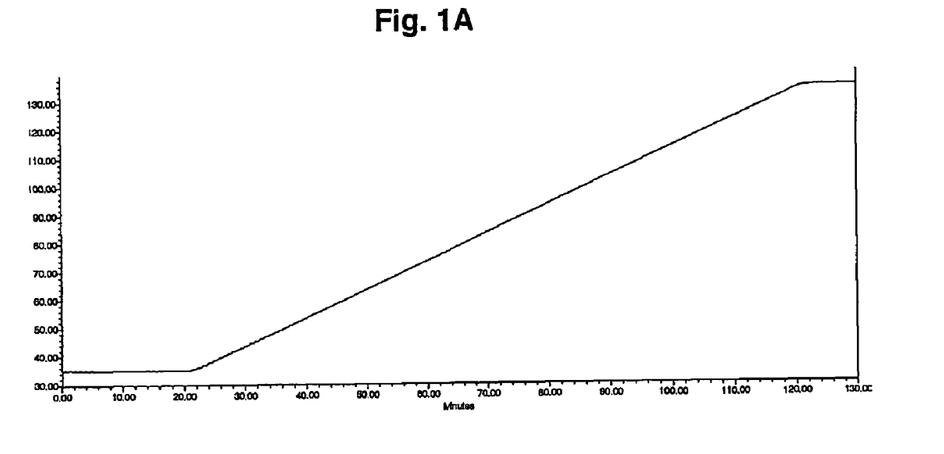
FIG. 1A represents the temperature profile used during the ATREF analysis of a low density polyethylene (LDPE) samples when using the 0.39×15 cm column packed with $Al_2O_3$.
Figure 1B:
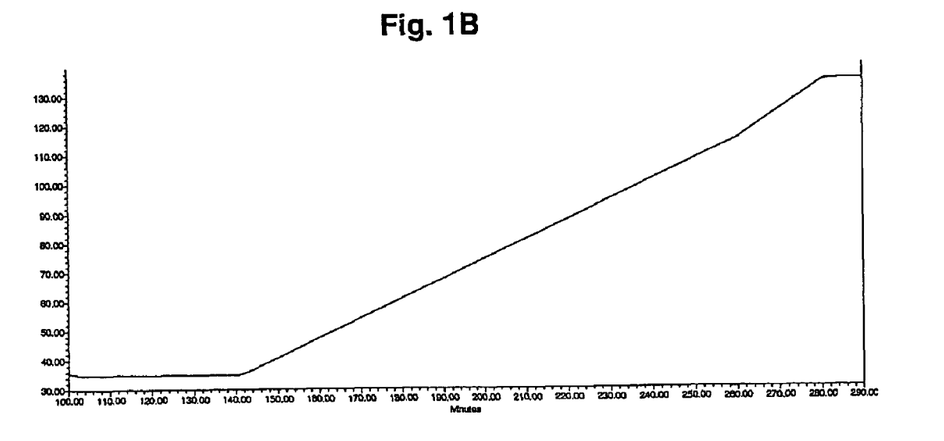
FIG. 1B represents the temperature profile used during the ATREF analysis of a LDPE sample when using the 0.8×25 cm stainless steel column packed with elastic wires made of stainless steel.

FIG. 1A represents the temperature profile used during the ATREF analysis of the polymer solutions when using the 0.39×15 cm column packed with $Al_2O_3$. FIG. 1B represents the temperature profile used during the ATREF analysis of the polyethylene solutions when using the 0.8×25 cm column packed with elastic wires. The temperature is comprised between 35° C. and 135° C.

Figure 2A:
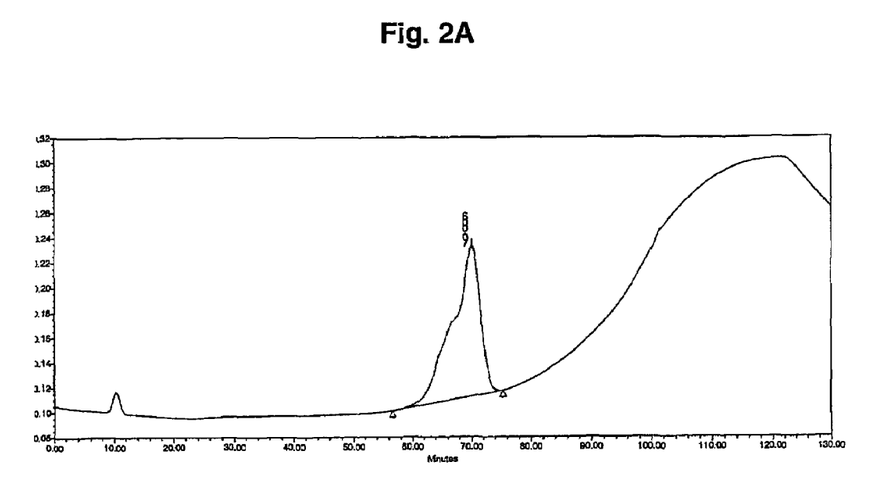
Figure 2B:
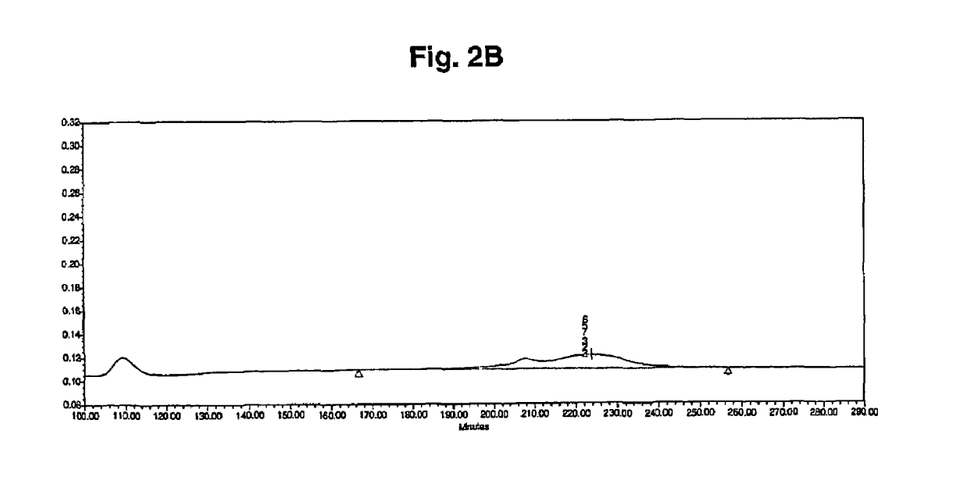
FIG. 2B represents the chromatogram of the LDPE sample obtained with the 0.8×25 cm stainless steel column packed with elastic wires made of stainless steel.
Figure 3:
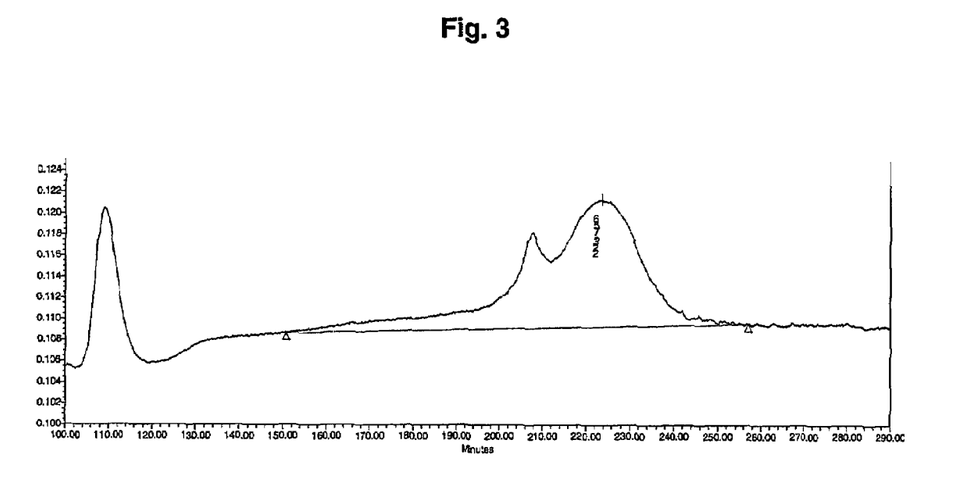
FIG. 3 is a zoomed view of the FIG. 2B, showing the chromatogram of the LDPE sample analyzed with ATREF method using a 0.8×25 cm stainless steel column packed with elastic wires made of stainless steel.

FIG. 2A represents the TREF chromatogram of the LDPE sample obtained with the 0.39×15 cm column packed with $Al_2O_3$, while FIG. 2B represents the TREF chromatogram of the LDPE sample obtained with the 0.8×25 cm column packed with elastic fibres according to the invention. As illustrated in FIG. 2A, a continuous shift of the baseline is observed which may be due to the decrease of the viscosity in the column with temperature rising between 35° C. to 135° C. The observed curvature of the baseline is detrimental to the quality of analysis and leads to a loss of information for the low temperature fractions of the sample, even for a high concentration of injected solution (6.3 mg/ml). However, as shown of FIG. 2B, the baseline variation of the DRI detector is greatly reduced when using the 0.8×25 cm stainless steel column packed with elastic wires made of stainless steel. Because of this baseline stability a zoom in the chromatogram can be represented in FIG. 3. In this chromatogram, the low temperature fractions, which exist in the sample at low concentrations, are clearly outlined. The intermediate temperature fractions are also better resolved, i.e. a peak at 207 minutes.

In conclusion, the column according to the invention enables to reduce baseline variation and provide very clear chromatograms, wherein low concentration fractions can be clearly identified.

Example 2

ATREF Analysis of a Polypropylene Sample

This example compares the analysis of a highly isotactic polypropylene (PP) sample, having an average tacticity of 98.7% and a weight average molecular weight of 460 kg/mol, when using a 0.8×25 cm stainless steel column packed with elastic wires or when using a traditional column. The 0.8×25 cm column is packed with elastic wires consisting of stainless steel wires having a diameter of 0.1 mm and an average length of 10 mm. The traditional column consists of a stainless steel column with 0.39 cm internal diameter and 15 cm in length and packed with small aluminium oxide particles having a 70-230 mesh-size. The PP sample was injected in the column packed with elastic wires at a concentration of 1.8 mg/ml. The PP sample was injected in the column packed with $Al_2O_3$ at a concentration of 5 mg/ml. As detector for ATREF, a built in differential refractive index (DRI) detector of a Waters GPC 150CV system is used.

Figure 4A:
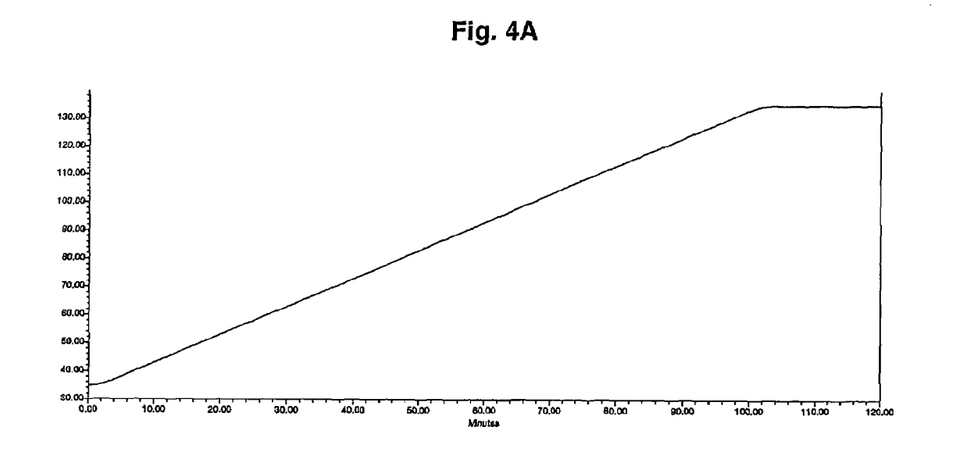
FIG. 4A represents the temperature profile used during the ATREF analysis of the polypropylene (PP) solutions when using the 0.39×15 cm column packed with $Al_2O_3$.
Figure 4B:
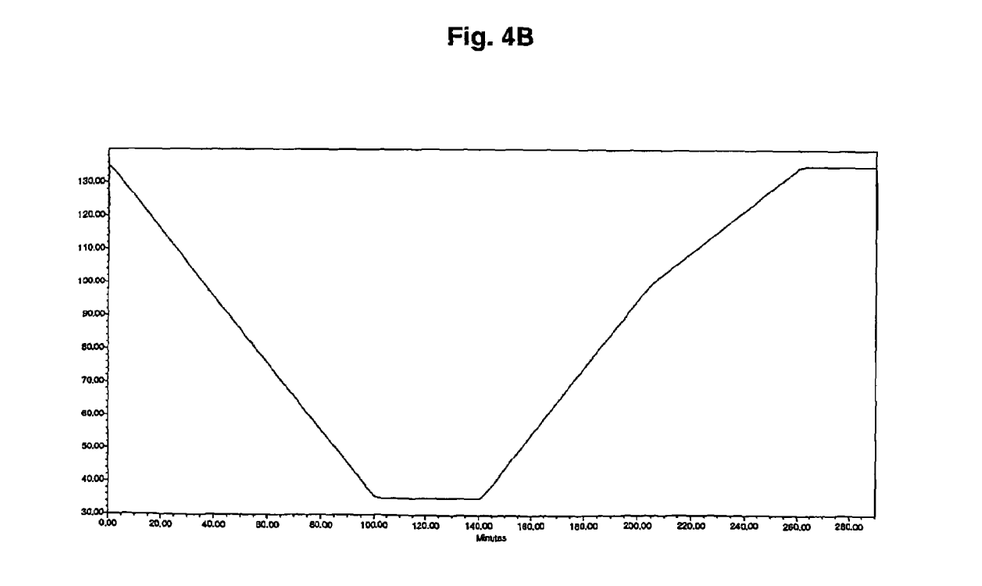
FIG. 4B represents the temperature profile used during the ATREF analysis of the PP solutions using the 0.8×25 cm stainless steel column packed with elastic wires made of stainless steel.

FIG. 4A represents the temperature profile used during the ATREF analysis of the polypropylene (PP) solutions when using the 0.39×15 cm column packed with $Al_2O_3$. FIG. 4B represents the temperature profile used during the ATREF analysis of the PP solutions using the 0.8×25 cm column packed with elastic wires. In both cases the temperature is comprised between 35° C. and 135° C.

Figure 5A:
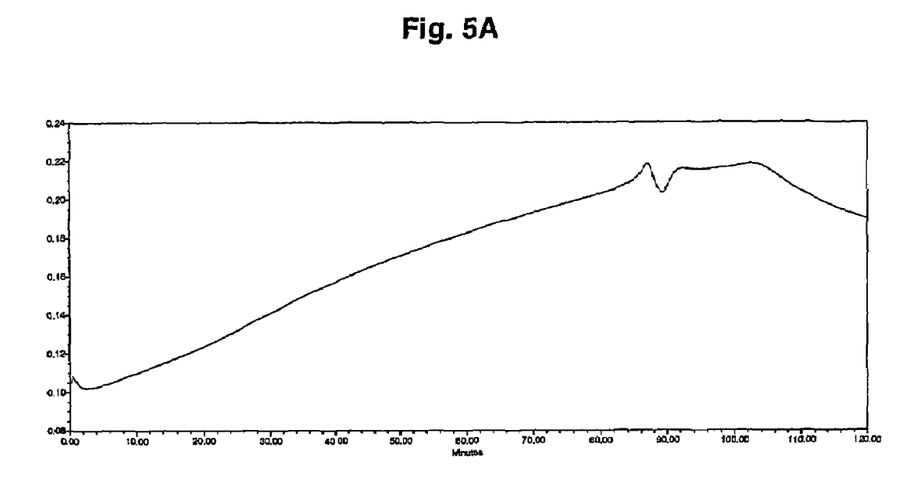
Figure 5B:
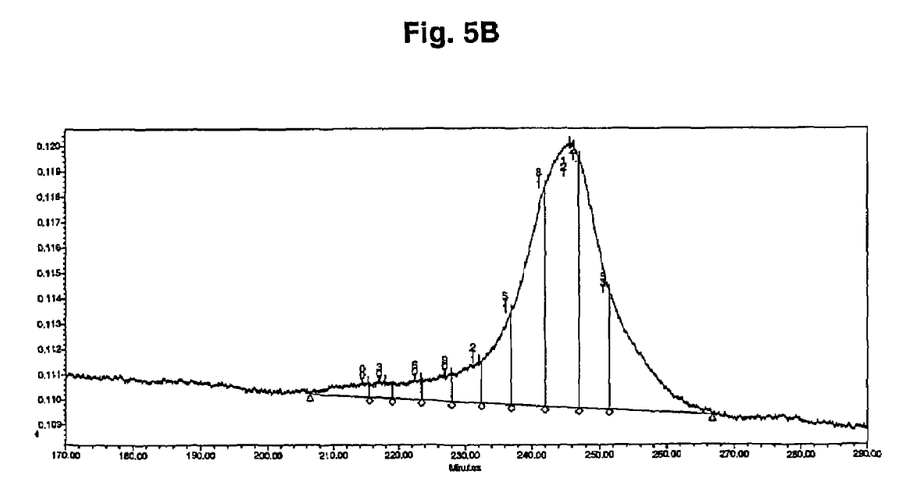
FIG. 5B represents the TREF chromatogram of the PP sample obtained with the 0.8×25 cm stainless steel column packed with elastic wires made of stainless steel.

FIG. 5A represents the TREF chromatogram of the PP sample analysed with the ATREF method using a 0.39×15 cm column packed with $Al_2O_3$, while FIG. 5B represents the TREF chromatogram of the PP sample analysed with the ATREF method using the 0.8×25 cm column packed with elastic wires. As illustrated in FIG. 5A, when using a column packed with $Al_2O_3$, a curvature of the baseline is obtained which is detrimental to the quality of analysis and the PP sample cannot be analysed. In contrast, the use of a column packed with elastic wires provides a clear chromatogram of the PP sample, as illustrated in FIG. 5B, wherein a temperature peak at 246 minutes is observed. The corresponding eluting temperature for this peak is 121° C.

In conclusion, the column according to the invention also enables to provide very clear chromatograms of polypropylene samples, which is very difficult when using traditional ATREF columns such as a column packed with $Al_2O_3$.

The invention claimed is:

1. Device for use in an analytical temperature rising elution fractionation analysis comprising a column characterized in that the packing of said column comprises elastic wires having a length per diameter (L/D) of at least 3, a temperature controlling system for controlling the temperature of said column, a sample injector for injecting a polymer sample solution into said column, a pump for eluting the polymer fractions from said column and a detector for detecting eluting fractions of said sample solution, wherein said detector is a differential refractive index (DRI) detector.

2. A method for performing an ATREF analysis of a crystalline or a semi-crystalline polymer solution comprising the steps of:
   injecting a sample of said polymer solution into a colunm characterized in that the packing of said column comprises elastic wires having a length per diameter (L/D) of at least 3;
   crystallizing said polymer sample solution in said colunm over a cooling temperature gradient to produce a crystallized polymer sample while keeping solvent flowing through said column;
   eluting said crystallized polymer sample by increasing the temperature of said column over a heating temperature gradient to produce eluted fractions of the polymer sample solution, said fractions being eluted in function of the temperature; and
   measuring the concentration of the eluted fractions of polymer sample solution by means of a detector.

3. Method according to claim 2, wherein the concentration of the eluted fractions of polymer sample solution are measured using a differential refractive index detector.

4. Method according to claim 2, wherein the column is provided in a temperature controlling system.

5. Method according to claim 2, wherein an amount of polymer lower than 2.0 mg polymer is injected into the column.

6. Method according to claim 2, wherein a volume of the polymer sample solution lower than 1.0 ml is injected into the column.

7. Method according to claim 2, wherein said polymer sample solution is injected automatically.

8. Method according to claim 7, wherein said polymer sample solution is injected automatically at a flow rate lower than 2.0 mL/min.

9. Method according to claim 2, wherein the crystallization of said polymer sample solution in said column is performed over a cooling temperature gradient with a maximum temperature below 210° C.

10. A method according to claim 2, wherein the crystallization of said polymer sample solution in said column is performed at a cooling rate higher than 0.5° C. per minute.

11. Method according to claim 2, wherein the elution of the crystallized polymer sample is performed over a heating temperature gradient with a maximum temperature up to 210° C.

12. Method according to claim 2, wherein the elution of the crystallized polymer sample is performed at a heating rate higher than 0.5° C. per minute.

* * * * *

UNITED STATES PATENT AND TRADEMARK OFFICE
CERTIFICATE OF CORRECTION

PATENT NO. : 7,389,678 B2
APPLICATION NO. : 10/530781
DATED : June 24, 2008
INVENTOR(S) : Boborodea et al.

It is certified that error appears in the above-identified patent and that said Letters Patent is hereby corrected as shown below:

Column 6, Line 53, "c) a column," should be changed to --(c) a column,--

Column 11, Line 28, "into a colunm" should be changed to --into a column--

Column 11, Line 32, "in said colunm" should be changed to --in said column--

Signed and Sealed this

Eighteenth Day of November, 2008

JON W. DUDAS
*Director of the United States Patent and Trademark Office*